(12) United States Patent
Catrone

(10) Patent No.: US 9,333,128 B2
(45) Date of Patent: May 10, 2016

(54) TRAUMA MANAGEMENT KIT HAVING EXTERNAL TOURNIQUET HOLSTER

(71) Applicant: TRIBALCO, LLC, Bethesda, MD (US)

(72) Inventor: Jeremy Catrone, Tampa, FL (US)

(73) Assignee: Tribalco, LLC, Bethesda, MD (US)

( * ) Notice: Subject to any disclaimer, the term of this patent is extended or adjusted under 35 U.S.C. 154(b) by 0 days.

(21) Appl. No.: 14/874,121

(22) Filed: Oct. 2, 2015

(65) Prior Publication Data
US 2016/0022512 A1    Jan. 28, 2016

Related U.S. Application Data

(63) Continuation of application No. PCT/US2014/030378, filed on Mar. 17, 2014.

(60) Provisional application No. 61/821,968, filed on May 10, 2013.

(51) Int. Cl.
| | | |
|---|---|---|
| *A61F 17/00* | (2006.01) | |
| *A61B 17/132* | (2006.01) | |
| *A61B 19/02* | (2006.01) | |
| *A45F 3/00* | (2006.01) | |

(52) U.S. Cl.
CPC . *A61F 17/00* (2013.01); *A45F 3/00* (2013.01); *A61B 17/132* (2013.01); *A61B 19/0264* (2013.01); *A61B 2019/028* (2013.01); *A61B 2019/0244* (2013.01)

(58) Field of Classification Search
CPC .. A61F 17/00; A61B 17/132; A61B 19/0264; A61B 2019/0244; A61B 2019/028; A45F 3/00
See application file for complete search history.

(56) References Cited

U.S. PATENT DOCUMENTS

| | | | | |
|---|---|---|---|---|
| 5,893,370 A | * | 4/1999 | Perez | A41D 13/0012 2/94 |
| 6,516,981 B2 | | 2/2003 | Perez et al. | |
| D689,281 S | * | 9/2013 | Blundell | D3/203.5 |
| 2010/0200627 A1 | * | 8/2010 | Shen | A45F 3/00 224/222 |
| 2011/0204114 A1 | * | 8/2011 | Miller | A45F 3/06 224/582 |
| 2012/0325880 A1 | * | 12/2012 | Yu | A45C 15/06 224/576 |
| 2014/0027480 A1 | * | 1/2014 | Van Heusen | A45F 5/02 224/191 |

FOREIGN PATENT DOCUMENTS

WO    WO2011-100074    8/2011

OTHER PUBLICATIONS

Police Press Releases, Eleven 10 Launches the Kydex TTH (Tactical Tourniquet Holder) for the SOFT-T, Jul. 26, 2012.
Soldier Systems—An industry Daily, New Holster Option for MRD Equipped Glocks, Aug. 24, 2011.
Safariland News in Tasco Hunting and Outdoors and Optical Australia Wide, Safariland® Launches New Series of Holsters with Cordura® Nylon Finish That Provide a Low Signature to Infrared Lighting, Jan. 15, 2013.
International Search Report and Written Opinion, dated Aug. 6, 2014, from corresponding International Application No. PCT/US2014/030378.

* cited by examiner

*Primary Examiner* — Corey Skurdal
(74) *Attorney, Agent, or Firm* — Greenberg Traurig, LLP

(57) ABSTRACT

A trauma management kit includes a main quick release bag for holding wound bandaging materials wherein the bag is made of a flexible nylon duck material, a rigid tourniquet holster fastened to an exterior surface of the quick release bag for receiving and holding a tourniquet therein for immediate access to the tourniquet without opening the main quick release bag. The holster preferably includes a two piece polymer case having an inner shell and an outer shell held together by rivets adjacent an upper opening of the case. A fabric holster cover made of nylon duck material is sewn to the exterior surface of the quick release bag over the holster to mitigate a near infrared signature of the polymer case.

5 Claims, 6 Drawing Sheets

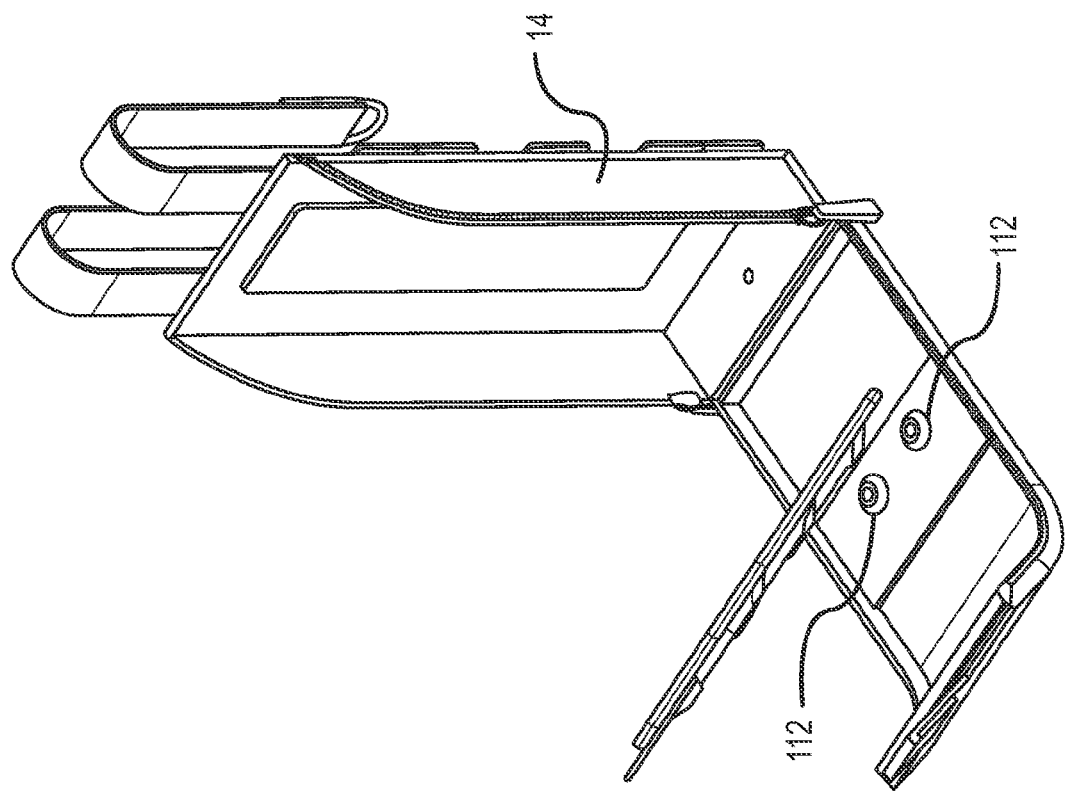

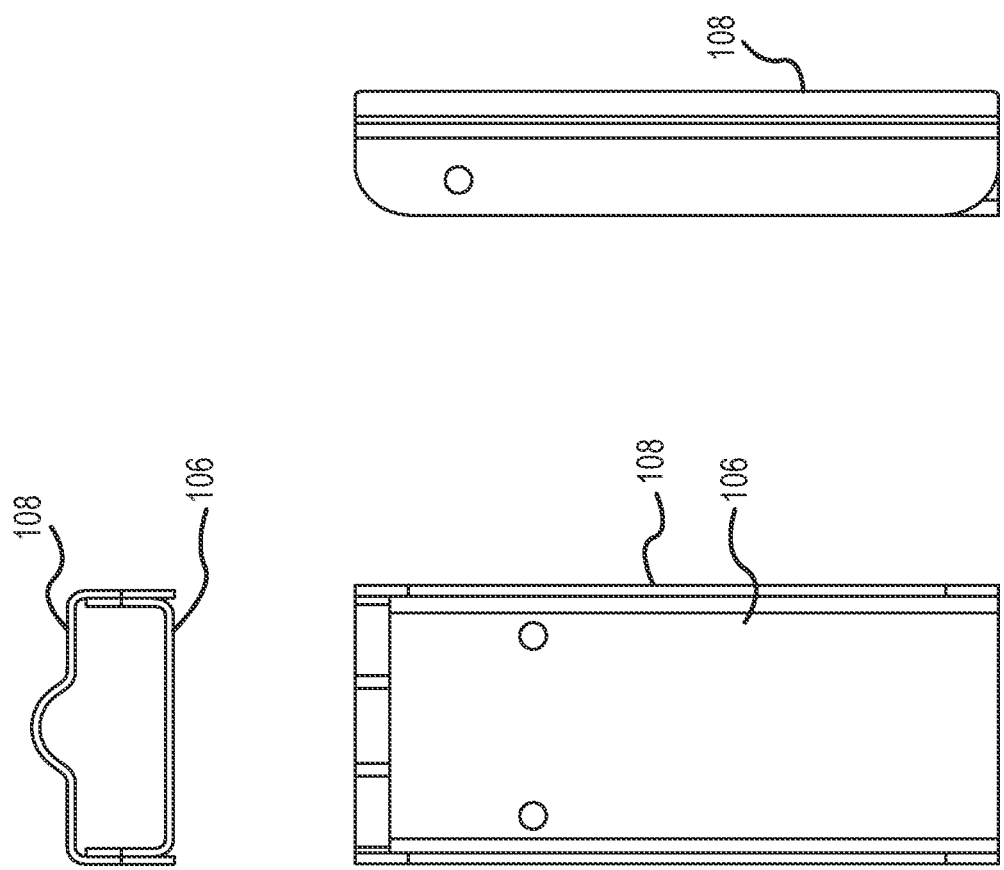

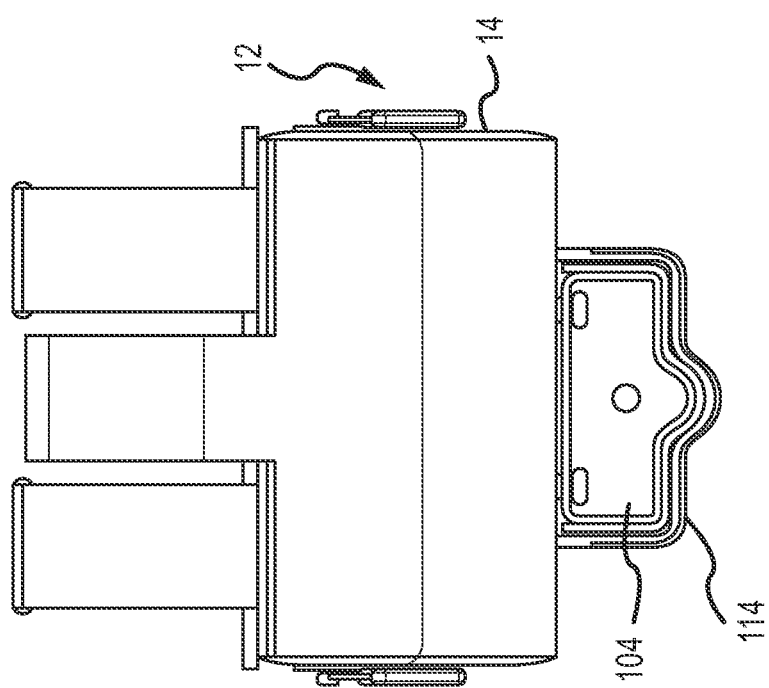

TRAUMA MANAGEMENT KIT HAVING EXTERNAL TOURNIQUET HOLSTER

CROSS REFERENCE TO RELATED APPLICATIONS

This application is a continuation of PCT application Serial Number PCT/US14/30378 filed Mar. 17, 2014, entitled Trauma Management Kit Having External Tourniquet Holster, which claims the benefit of priority of U.S. provisional patent application Ser. No. 61/821,968 filed May 10, 2013, the content of both of which are incorporated by reference in their entirety.

BACKGROUND OF THE DISCLOSURE

1. Field of the Disclosure

The present disclosure relates to tourniquet holders. In particular, it relates to a permanent adherence to a trauma management kit that is configured for quick retrieval of a tourniquet for use in battlefield environments in which efficiency of movement is critical to survivability.

2. State of the Art

Trauma medical kits carried by soldiers in the battle space include many items such as gauze, scissors, bandages, tourniquets, etc. However, in the vast majority of casualty situations, it is a tourniquet that is needed first to prevent life threatening blood loss. Currently there is no practical way for a soldier to co-locate his/her tourniquet within their trauma medical kit, and gain access to that tourniquet, without taking additional steps to manipulate the kit. These additional steps cost valuable time; and under stress prove difficult to complete.

SUMMARY OF THE DISCLOSURE

A holster for secure provisioning of a tourniquet such as a SOFTT, SOFFT-Wide or CAT tourniquet for instant, one handed, access from a trauma management kit is disclosed. In one embodiment, a trauma management kit with a main quick release bag for holding wound bandaging materials, a rigid tourniquet holster shaped for receiving and holding a commercially available tourniquet therein for immediate access to the tourniquet without opening the main quick release bag, and a holster cover enclosing the holster. The quick release bag is made of a flexible material. The flexible material may be nylon duck. The quick release bag may further include holes in an outer shell of the quick release bag, where the holes are designed for receiving rivets. The holster is fastened to an exterior surface of the quick release bag and comprises a two piece polymer case having an inner shell and an outer shell held together by rivets adjacent an upper opening of the case. The holster may be fastened to the outer shell of the quick release bag with rivets, the rivets being attached to the holster and passing through the holes in the outer shell of the quick release bag. The holster is replaceable with a different holster configured to receive and hold another commercially available tourniquet. The holster cover mitigates a near infrared signature of the polymer case. The holster cover may be permanently or removably attached to the holster, and may be made of a flexible nylon duck material. In another embodiment, the holster cover may be sewn to the exterior surface of the quick release bag and contains the holster within.

In another embodiment, a trauma management kit including a main quick release bag for holding wound bandaging materials made of a flexible nylon duck material, a rigid tourniquet holster shaped for receiving and holding a commercially available tourniquet therein for immediate access to the tourniquet without opening the main quick release bag, and a nylon duck holster cover sewn to the exterior surface of the quick release bag. The quick release bag further includes holes in an outer shell of the bag for receiving rivets. The holster comprises a two piece polymer case having an inner shell and an outer shell held together by rivets adjacent an upper opening of the case, the outer shell having a rounded, raised portion that extends vertically from top to bottom along a midline of the outer shell. The holster is fastened to an exterior surface of the quick release bag with rivets that are attached to the holster and pass through the holes in the outer shell of the quick release bag. The holster is replaceable with a different holster configured to receive and hold another commercially available tourniquet. The holster cover encloses the polymer case, and the holster cover mitigates a near infrared signature of the polymer case.

BRIEF DESCRIPTION OF THE DRAWINGS

The disclosure will be better understood and objects, other than those set forth above, will become apparent when consideration is given to the following detailed description. Such description makes reference to the accompanying drawings wherein:

FIG. 3 is an open view of the main bag of the trauma kit case shown in FIG. 2.

FIG. 4 is a separate perspective view of one embodiment of a hard polymer holster utilized in the trauma kit in accordance with the present disclosure.

FIG. 5 is a top view of the assembled trauma kit case shown in FIG. 2.

DETAILED DESCRIPTION

In the following description, numerous specific details are set forth in order to provide a more thorough disclosure. It will be apparent, however, to one skilled in the art, that the art disclosed may be practiced without these specific details. In some instances, well-known features may have not been described in detail so as not to obscure the art disclosed.

Figure 1:
FIG. 1 shows a back perspective view of a soldier wearing a trauma kit incorporating an embodiment of the present disclosure.

A soldier 10 is shown in FIG. 1 wearing a vest to which a trauma management kit 12 is attached, that the soldier 10 can easily grasp and open. This trauma management kit 12 encloses a variety of tools and bandage materials (not visible) in a quick open canvas bag 14 that has a tourniquet holster 100 in accordance with the present disclosure attached to the outer surface of the quick release bag 14. This permits the tourniquet 102 to be immediately withdrawn for immediate use even before the quick release bag 14 is opened in the event of wounding to the soldier or soldier nearby.

In the event of massive trauma, instant access to the tourniquet 102 can mean the difference between life and death to an injured soldier. As can readily be seen in FIG. 1, the tourniquet 102 in the holster 100 is immediately available in such an event.

Figure 2:
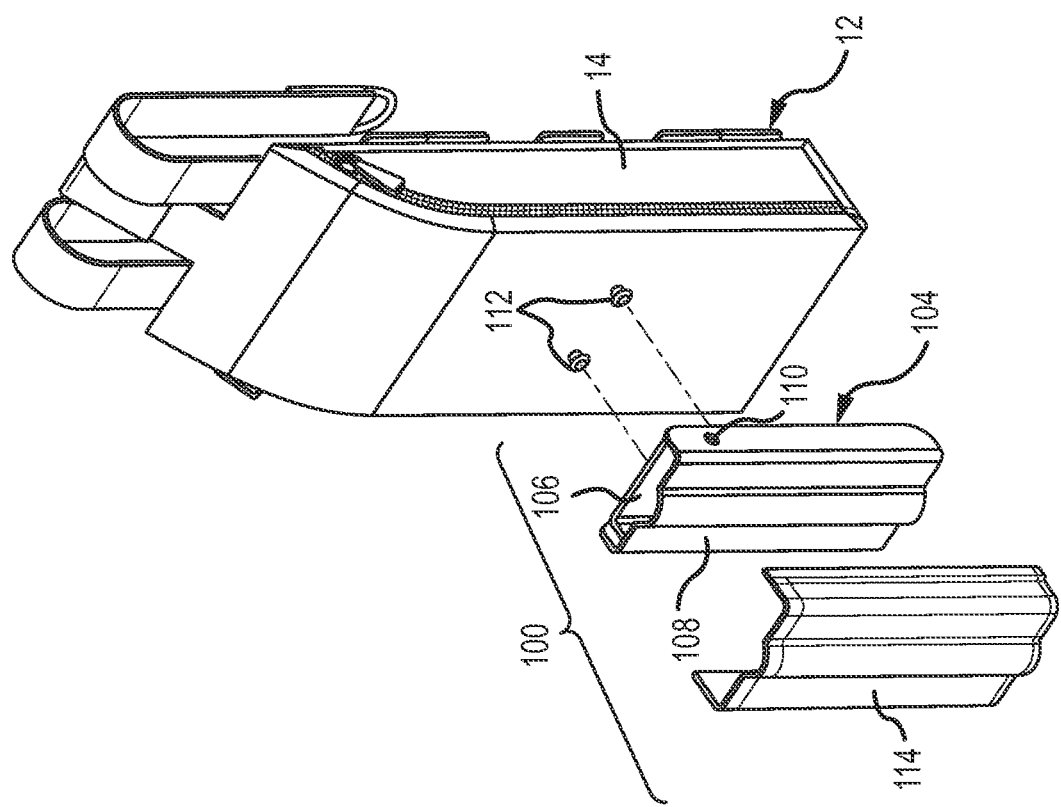
FIG. 2 is a perspective exploded view of the trauma kit case shown on the soldier in FIG. 1.

FIG. 2 is a separate view of the management kit 12 with the tourniquet holster 100 exploded in perspective. The holster 100 comprises a two-piece polymer case 104 into which a tourniquet 102 can be placed (not shown). The polymer case 104 is preferably made of a thermoplastic polymeric material such as Kydex and has an inner shell 106 and outer shell 108 that are held together by rivets 110 adjacent the upper opening of the case. Another set of two rivets 112 fastens the plastic case 104 to the outer surface of the main bag 14 of the kit 12. An outer fabric cover 114, preferably a nylon canvas duck fabric, may optionally then be sewn to the outer surface of the main bag 14 of the kit 12 to enclose the plastic case 104. The outer fabric cover 114 may optionally be attached, permanently or removably, to the holster case 104.

The rivets 112 that are used to fasten the plastic case 104 to the outer surface of the kit bag 14 are one piece rivets. Each rivet, preferably made of aluminum, is inserted through a hole in the inner shell 106 of the plastic case 104 so as to project toward the main bag 1. The rivets 112 are then inserted through corresponding holes in the outer shell of the main bag 14. A plier type tool is then used to expand the protruding end of each rivet against the inner surface of the outer shell of the main bag 14. FIG. 3 shows the rivet configuration inside the main bag 14 of the kit 12.

Figure 7:
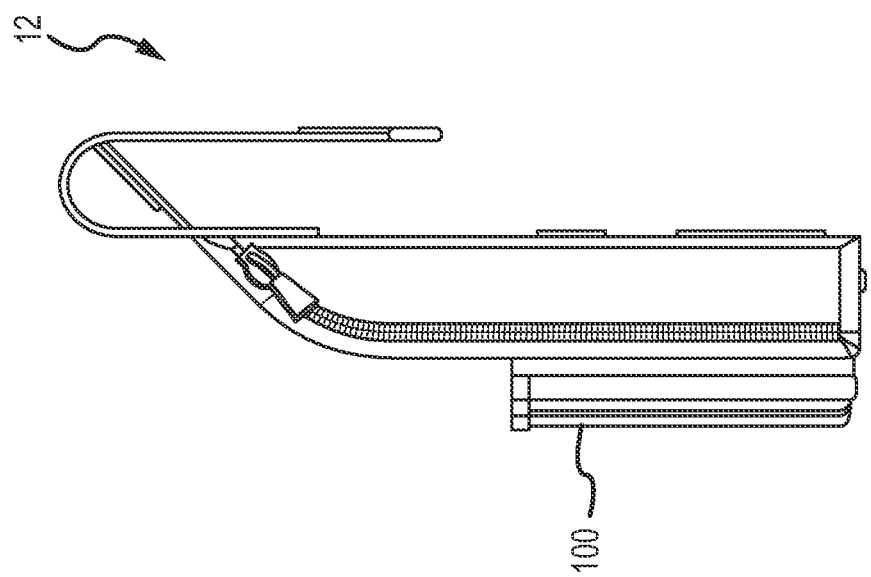
FIG. 7 is a side view of the kit shown in FIG. 2.
Figure 6:
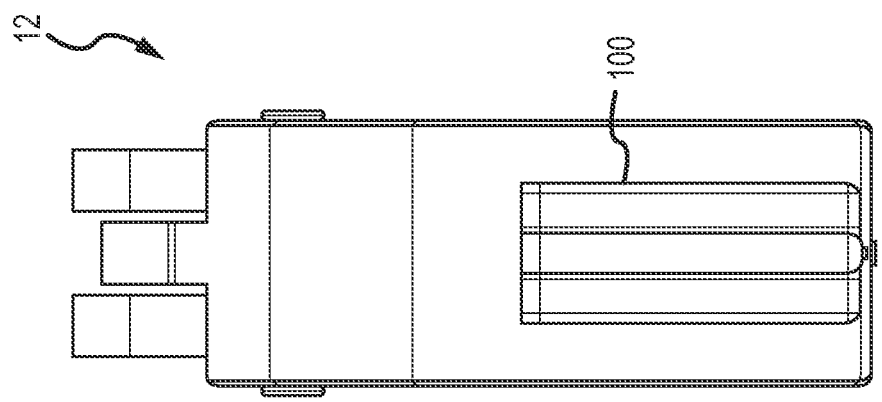
FIG. 6 is a front plan view of a trauma kit shown in FIG. 2

A perspective view of the thermoplastic case 104 for one type of tourniquet is shown in FIG. 4 along with top, back and side views of the case 104. A top view of the assembled kit 12 is shown in FIG. 5. A front view and side view of the assembled kit 12 is shown in FIGS. 6 and 7.

Currently there are three commercially available tourniquets 102. Preferably a different holster case 104 shape will be provided for each style of tourniquet to ensure that each type is securely held in the holster 100 until needed. The holster case 104 is interchangeable with another holster case (not pictured), and therefore a holster case 104 for one commercially available tourniquet may be replaced with a holster case (not pictured) designed for another commercially available tourniquet.

Finally, it will also be apparent to one skilled in the art that many variations to the kit configuration may be made. For example, a kit 12 may be provided with more than one holster 100 on its outer cover depending on the overall size of the main bag 14 of the kit 12. Accordingly, it is intended that the art disclosed shall be limited only to the extent required by the appended claims and the rules and principles of applicable law.

I claim:

1. A trauma management kit comprising:
   a main quick release bag for holding wound bandaging materials wherein the bag is made of a flexible material;
   a rigid tourniquet holster shaped for receiving and holding a commercially available tourniquet therein for immediate access to the tourniquet without opening the main quick release bag, the holster being fastened to an exterior surface of the quick release bag and comprising a two piece polymer case having an inner shell and an outer shell held together by rivets adjacent an upper opening of the case, the holster being replaceable with a different holster configured to receive and hold another commercially available tourniquet; and
   a holster cover enclosing the holster, wherein the cover mitigates a near infrared signature of the polymer case.

2. The trauma management kit of claim 1 wherein the quick release bag has holes in an outer shell of the quick release bag for receiving rivets, wherein the holster is fastened to the outer shell with rivets that are attached to the holster and pass through the holes in the outer shell.

3. The trauma management kit of claim 1 wherein the flexible material and the holster cover are nylon duck.

4. The trauma management kit of claim 1 wherein the holster cover is sewn to the exterior surface of the quick release bag and contains the holster.

5. A trauma management kit comprising:
   a main quick release bag for holding wound bandaging materials made of a flexible nylon duck material, the bag having holes in an outer shell of the bag for receiving rivets;
   a rigid tourniquet holster shaped for receiving and holding a commercially available tourniquet therein for immediate access to the tourniquet without opening the main quick release bag, the holster being fastened to an exterior surface of the quick release bag with rivets that are attached to the holster and pass through the holes in the outer shell of the quick release bag, the holster comprising a two piece polymer case having an inner shell and an outer shell held together by rivets adjacent an upper opening of the case, the outer shell having a rounded, raised portion that extends vertically from top to bottom along a midline of the outer shell, the holster being replaceable with a different holster configured to receive and hold another commercially available tourniquet; and
   a nylon duck holster cover sewn to the exterior surface of the quick release bag, the holster cover enclosing the polymer case, and the holster cover mitigating a near infrared signature of the polymer case.

* * * * *

UNITED STATES PATENT AND TRADEMARK OFFICE
CERTIFICATE OF CORRECTION

PATENT NO. : 9,333,128 B2
APPLICATION NO. : 14/874121
DATED : May 10, 2016
INVENTOR(S) : Catrone et al.

Page 1 of 1

It is certified that error appears in the above-identified patent and that said Letters Patent is hereby corrected as shown below:

On the Title Page

Item (12) "Catrone" should read -- Catrone, et al. --.

Item (72) Inventor is corrected to read:
-- Jeremy Catrone, Tampa, (FL);
Grant Derrick, Pinehurst, (NC) --.

Signed and Sealed this
Third Day of December, 2019

Andrei Iancu
*Director of the United States Patent and Trademark Office*